United States Patent [19]

Austel et al.

[11] Patent Number: 4,746,658
[45] Date of Patent: May 24, 1988

[54] 2-PHENYL-IMIDAZO-PYRAZINES, -PYRIDAZINES AND -TRIAZINES

[75] Inventors: Volkhard Austel; Norbert Hauel, both of Biberach; Joachim Heider, Warthausen; Manfred Reiffen, Biberach; Jacobus C. A. Van Meel, Biberach; Willi Diederen, Biberach, all of Fed. Rep. of Germany

[73] Assignee: Dr. Karl Thomae GmbH, Biberach, Fed. Rep. of Germany

[21] Appl. No.: 71,329

[22] Filed: Jul. 9, 1987

Related U.S. Application Data

[60] Continuation of Ser. No. 905,484, Sep. 8, 1986, abandoned, which is a division of Ser. No. 675,299, Nov. 27, 1984, Pat. No. 4,656,171.

[30] Foreign Application Priority Data

Dec. 23, 1983 [DE]  Fed. Rep. of Germany ....... 3346640

[51] Int. Cl.$^4$ ..................... A61K 31/50; C07D 487/04
[52] U.S. Cl. ..................................... 514/248; 544/236
[58] Field of Search ......................... 544/236; 514/248

[56] References Cited

U.S. PATENT DOCUMENTS 4,477,454  10/1984  Jonas et al. ..................... 544/236 X

*Primary Examiner*—Donald G. Daus
*Assistant Examiner*—William A. Teoli, Jr.
*Attorney, Agent, or Firm*—Weissenberger, Hammond & Littell

[57] ABSTRACT

Compounds of the formula

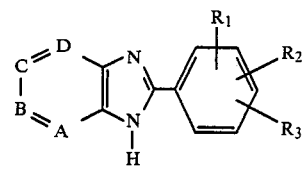

wherein

A, B, C and D are each independently —N= or —CH=, provided, however, that at least two of them must be —N=, and when A and C are both —N=, at least one or both of B and D must be —N=; and $R_1$, $R_2$ and $R_3$ are substituents of diverse types;

tautomers thereof; and non-toxic, pharmacologically acceptable acid addition salts thereof. The compounds are useful as cardiotonics.

13 Claims, No Drawings

2-PHENYL-IMIDAZO-PYRAZINES, -PYRIDAZINES AND -TRIAZINES

This is a continuation of application Ser. No. 905,484, filed Sept. 8, 1986, now abandoned, which is a division of application Ser. No. 675,299 filed Nov. 27, 1984 now U.S. Pat. No. 4,656,171.

This invention relates to novel imidazole derivatives and non-toxic acid addition salts thereof, to methods of preparing these compounds, to pharmaceutical compositions containing them, and to a method of using them as cardiotonics.

THE PRIOR ART

Published European Application No. 24,290 discloses certain 2-phenyl-imidazole derivatives having useful pharmacodynamic properties.

THE INVENTION

More particularly, the present invention relates to a novel class of imidazole derivatives of the formula

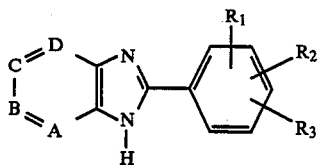

wherein

A, B, C and D are each independently —N= or —CH=, provided, however, that at least two of them must be —N=, and when A and C are both —N=, at least one or both of B and D must be —N=;

$R_1$ is halogen, alkyl, cyano, amino, alkylamino, benzyloxy, aminocarbonyl, alkylaminocarbonyl, dialkylaminocarbonyl, carboxyl, alkoxycarbonyl, alkylsulfonyloxy, alkylsulfonyl, aminosulfonyl, alkylaminosulfonyl, dialkylaminosulfonyl, nitro, alkanoylamino, alkylsulfonylamino or N-alkylsulfonylamino; or, when 3 to 4 of A, B, C and D are —N= and 0 to 1 of A, B, C and D are —CH=, or, when A and B are both —N= and C and D are both —CH=, $R_1$ may also be hydrogen, hydroxyl, alkoxy, phenylalkoxy, alkylmercapto, alkylsulfinyl, dialkylamino, cyanoalkoxy, alkenyloxy or alkynyloxy;

$R_2$ and $R_3$, which may be identical to or different from each other, are each independently hydrogen, halogen, alkyl, hydroxyl, alkoxy, phenylalkoxy, alkylmercapto, alkylsulfinyl, alkylsulfonyl, aminosulfonyl, alkylaminosulfonyl, dialkylaminosulfonyl, alkylsulfonyloxy, alkylsulfonylamino, N-alkyl-alkylsulfonylamino, nitro, amino, alkylamino, dialkylamino, cyanoalkoxy, cyano, carboxyl, alkoxycarbonyl, aminocarbonyl, alkylaminocarbonyl, dialkylaminocarbonyl, N-alkanoylamino, alkenyloxy or alkynyloxy;

tautomers thereof; and non-toxic, pharmacologically acceptable acid additiion salts thereof.

The terms "alkyl" and "alkoxy" as used herein refer to alkyl of 1 to 3 carbon atoms and alkoxy of 1 to 3 carbon atoms, respectively.

The terms "alkenyl" and "alkynyl" as used herein refer to alkenyl of 3 to 5 carbon atoms and alkynyl of 3 to 5 carbon atoms, respectively.

The present invention thus relates to novel imidazo[4,5-b]pyrazines, imidazo[4,5-c]pyridazines, imidazo[4,5-d]pyridazines, imidazo[4,5-d]-1,2,3-triazines, imidazo[4,5-e]-1,2,4-triazines and imidazo[4,5-e]tetrazines of the formula I above, tautomers and acid addition salts thereof, particularly non-toxic, pharmacologically acceptable acid addition salts with inorganic or organic acids, pharmaceutical compositions containing these compounds and processes for preparing them.

Specific examples of variable substituents $R_1$, $R_2$ and $R_3$ in formula I above are the following:

Hydrogen, fluorine, chlorine, bromine, methyl, ethyl, n-propyl, isopropyl, hydroxyl, methoxy, ethoxy, n-propoxy, isopropoxy, benzyloxy, 1-phenylethoxy, 1-phenyl-n-propoxy, 1-methyl-1-phenyl-ethoxy, 2-phenyl-ethoxy, 3-phenyl-n-propoxymethylmercapto, ethylmercapto, n-propylmercapto, methylsulfinyl, ethylsulfinyl, isopropylsulfinyl, methylsulfonyl, ethylsulfonyl, n-propylsulfonyl, aminosulfonyl, methylaminosulfonyl, ethylaminosulfonyl, n-propylaminosulfonyl, dimethylaminosulfonyl, diethylaminosulfonyl, diisopropylaminosulfonyl, ethylmethylaminosulfonyl, methylsulfonyloxy, ethylsulfonyloxy, n-propylsulfonyloxy, methylsulfonylamino, ethylsulfonylamino, isopropylsulfonylamino, N-methyl-methylsulfonylamino, N-ethyl-methylsulfonylamino, N-methyl-ethylsulfonylamino, N-n-propyl-ethylsulfonylamino, N-methyl-n-propylsulfonylamino, N-ethyl-isopropylaminosulfonyl, amino, methylamino, ethylamino, n-propylamino, isopropylamino, dimethylamino, diethylamino, di-n-propylamino, N-ethyl-methylamino, N-methyl-isopropylamino, cyanomethoxy, 1-cyanoethoxy, 2-cyanoethoxy, 3-cyanopropoxy, cyano, nitro, carboxyl, methoxycarbonyl, ethoxycarbonyl, n-propoxycarbonyl, isopropoxycarbonyl, aminocarbonyl, methylaminocarbonyl, ethylaminocarbonyl, isopropylaminocarbonyl, dimethylaminocarbonyl, diethylaminocarbonyl, di-n-propylaminocarbonyl, N-ethyl-methylaminocarbonyl, N-ethyl-n-propylaminocarbonyl, N-formylamino, N-acetylamino, N-propionylamino, allyloxy, but-2-enyloxy, pent-2-enyloxy, propargyloxy, but-2-ynyloxy or pent-2-ynyloxy.

A preferred subgenus is constituted by those compounds of the formula I
wherein 2 to 3 of A, B, C and D are —N= and the others are —CH=, provided, however, that when A and C are both —N= one of B and D must also be —N=;

$R_1$ and $R_2$ are each individually halogen, methyl, methoxy, benzyloxy, ethoxy, propoxy, dimethylamino, amino, aminocarbonyl, aminosulfonyl, methylaminosulfonyl, dimethylaminosulfonyl, cyano, nitro, methylmercapto, methylsulfinyl, methylsulfonyl, methanesulfonyloxy, methanesulfonylamino, N-methylmethanesulfonylamino, propargyloxy or cyanomethoxy; and $R_3$ is hydrogen, dimethylamino, methoxy, ethoxy, propoxy or methylmercapto;

tautomers thereof; and non-toxic, pharmacologically acceptable acid addition salts thereof.

The compounds embraced by formula I may be prepared by the following methods:

Method A

By cyclizing a compound of the formula

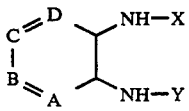

(II)

wherein

A, B, C and D have the meanings previously defined, and one of X and Y is hydrogen and the other or both are

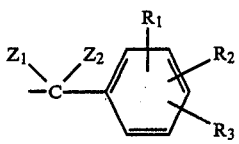

where $R_1$, $R_2$ and $R_3$ have the meanings previously defined, and $Z_1$ and $Z_2$ are each independently halogen, optionally substituted amino, or hydroxyl or mercapto optionally substituted by lower alkyl; or $Z_1$ and $Z_2$ together are oxygen or sulfur, imino optionally mono- or disubstituted by alkyl of 1 to 3 carbon atoms, or alkylenedioxy or alkylenedithio of 2 to 3 carbon atoms.

The compound of the formula II may be prepared separately or in situ in the reaction mixture.

The cyclization is advantageously carried out in a solvent or mixture of solvents such as ethanol, isopropanol, glacial acetic acid, benzene, chlorobenzene, toluene, xylene, glycol, glycol monomethyl ether, diethylene glycol dimethyl ether, sulfolane, dimethylformamide or tetralin, or in an excess of the acylating agent used to prepare the compound of the general formula II, such as in the corresponding nitrile, anhydride, acid halide, ester, amide or methoiodide, for example at temperatures between 0° and 250° C., but preferably at the boiling point of the reaction mixture, optionally in the presence of a condensing agent such as phosphorus oxychloride, thionyl chloride, sulfuryl chloride, sulfuric acid, p-toluenesulfonic acid, hydrochloric acid, phosphoric acid, polyphosphoric acid or acetic acid anhydride, or optionally also in the presence of a base such as sodium hydroxide, potassium hydroxide, potassium ethoxide or potassium tert.butoxide. However, cyclization may also be carried out without a solvent and/or condensing agent.

Method B

For the preparation of a compound of the formula I wherein at least one of $R_1$, $R_2$ and $R_3$ is alkylsulfinyl or alkylsulfonyl:

By oxidizing a compound of the formula

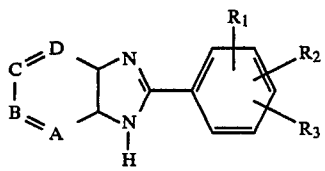

(III)

wherein A, B, C, D, $R_1$, $R_2$ and $R_3$ have the meanings previously defined, but at least one of $R_1$, $R_2$ and $R_3$ is (alkyl of 1 to 3 carbon atoms)mercapto or (alkyl of 1 to 3 carbon atoms)sulfinyl.

The oxidation is preferably carried out in a solvent or mixture of solvents, for instance, in water, water/pyridine, acetone, glacial acetic acid, dilute sulfuric acid or trifluoroacetic acid, at temperatures between −80° and 100° C., depending on the oxidizing agent which is used.

In order to prepare an alkylsulfinyl compound of the formula I the oxidation is carried out with one equivalent of the oxidizing agent, for example with hydrogen peroxide in glacial acetic acid, trifluoroacetic acid or formic acid at 0° to 20° C. or in acetone at 0° to 60° C.; with a peracid such as performic acid in glacial acetic acid or trifluoroacetic acid at 0° to 50° C.; with m-chloroperbenzoic acid in methylene chloride or chloroform at −20° to 60° C.; with sodium metaperiodate in aqueous methanol or ethanol at −15° to 25° C.; with bromine in glacial acetic acid or aqueous acetic acid optionally in the presence of a base such as sodium acetate; with N-bromosuccinimide in ethanol; with tert.butyl hypochlorite in methanol at −80° to −30° C.; with iodobenzodichloride in aqueous pyridine at 0° to 50° C.; with nitric acid in glacial acetic acid at 0° to 20° C.; with chromic acid in glacial acetic acid or in acetone at 0° to 20° C.; or with sulfuryl chloride in methylene chloride at −70° C., followed by the hydrolysis of the resultant thioether-chlorine complex with aqueous ethanol.

In order to prepare an alkylsulfonyl compound of the formula I, the oxidation is carried out with one or with two or more equivalents of the oxidizing agent which is used, for instance, with hydrogen peroxide in glacial acetic acid, trifluoroacetic acid or in formic acid at 20° to 100° C. or in acetone at 0° to 60° C.; with a peracid such as a performic acid or m-chloroperbenzoic acid in glacial acetic acid, trifluoroacetic acid, methylene chloride or chloroform at temperatures between 0° and 60° C.; with nitric acid in glacial acetic acid at 0° to 20° C.; or with chromic acid or potassium permanganate in glacial acetic acid, water/sulfuric acid or in acetone at 0° to 20° C.

Method C

For the preparation of a compound of the formula I wherein at least one of $R_1$, $R_2$ and $R_3$ is alkylsulfonyloxy, alkylsulfonylamino, N-alkyl-alkylsulfonylamino or alkanoylamino:

By reacting a compound of the formula

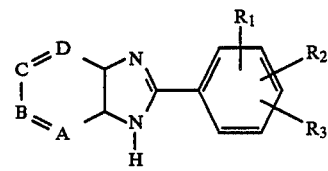

(IV)

wherein A, B, C, D, $R_1$, $R_2$ and $R_3$ have the meanings previously defined, but at least one of $R_1$, $R_2$ and $R_3$ must be hydroxyl, amino or (alkyl of 1 to 3 carbon atoms)amino, with an acid of the formula $$R_4—WOH \quad (V)$$

wherein $R_4$ is alkyl of 1 to 3 carbon atoms, and

W is sulfonyl or carbonyl, in the presence of a dehydrating agent and/or an agent which activates the acid or the amine, or with a reactive derivative thereof.

The reaction is advantageously carried out in a solvent or mixture of solvents such as methylene chloride, ether, tetrahydrofuran, dioxane, water or benzene, optionally in the presence of an acid-binding agent such as sodium carbonate, sodium hydroxide, triethylamine or pyridine, where the latter two may simultaneously also be used as solvents, in the presence of an acid-activating or dehydrating agent such as thionyl chloride or phosphorus pentachloride, but preferably with a reactive derivative of a compound of the formula V, for instance with the anhydride or halide thereof such as methanesulfonyl chloride or ethanesulfonyl chloride, preferably at temperatures between 0° and 100° C., for example at temperatures between room temperature and 50° C.

Method D

For the preparation of a compound of the formula I wherein at least one of $R_1$, $R_2$ and $R_3$ is carbonyl or sulfonyl substituted by an amino, alkylamino or dialkylamino:

By reacting a compound of the formula

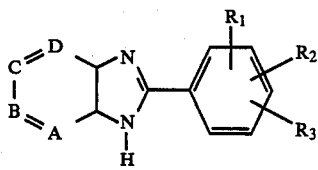

(VI)

wherein A, B, C, D, $R_1$, $R_2$ and $R_3$ have the meanings previously defined, but at least one of $R_1$, $R_2$ and $R_3$ must be carboxyl or hydroxysulfonyl, or a reactive derivative thereof, with an amine of the formula

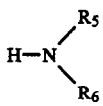

(VII)

wherein $R_5$ and $R_6$ are each independently hydrogen or alkyl of 1 to 3 carbon atoms, or with a reactive derivative thereof.

The reaction is advantageously carried out in a solvent or mixture of solvents such as methylene chloride, chloroform, carbon tetrachloride, ether, tetrahydrofuran, dioxane, benzene, toluene, acetonitrile or dimethylformamide, optionally in the presence of an acid-activating agent or a dehydrating agent, for instance in the presence of ethyl chloroformate, thionyl chloride, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole or N,N'-thionyldiimidazole or triphenylphosphine/carbon tetrachloride, or in the presence of an agent which activates the amino group, such as phosphorus trichloride, and optionally in the presence of an inorganic base such as sodium carbonate or a tertiary organic base such as triethylamine or pyridine, which may simultaneously act as the solvent, at temperatures between −25° and 250° C., but preferably at temperatures between −10° C. and the boiling point of the solvent which is used. Moreover, any water formed during the reaction may be removed by azeotropic distillation, for instance by heating with toluene, using a water trap or by adding a drying agent such as magnesium sulfate or a molecular sieve.

However, it is particularly advantageous to carry out the reaction in a corresponding halide, such as the carboxylic or sulfonic acid chloride, and a corresponding amine, which may simultaneously serve as the solvent, at temperatures between 0° and 50° C.

Method E

For the preparation of a compound of the formula I wherein at least one of $R_1$, $R_2$ and $R_3$ is cyanoalkoxy, alkenyloxy or alkynyloxy or one or both of $R_2$ and $R_3$ are alkoxy:

By reacting a compound of the formula

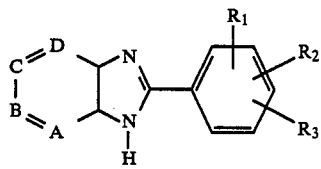

(VIII)

wherein A, B, C, D, $R_1$, $R_2$ and $R_3$ have the meanings previously defined, but at least one of $R_1$, $R_2$ and $R_3$ must be hydroxyl, with a compound of the formula $$R_7-U \qquad (IX)$$

wherein $R_7$ is alkyl of 1 to 3 carbon atoms optionally substituted by cyano, alkenyl or alkynyl of 3 to 5 carbon atoms, and U is a nucleophilic leaving group such as halogen, substituted sulfonyloxy or alkoxysulfonyloxy.

The reaction is carried out with a corresponding alkylating agent such as methyl iodide, ethyl iodide, diethyl sulfate, dimethylsulfate, chloroacetonitrile, allyl bromide or propargyl bromide, advantageously in a solvent or mixture of solvents such as methylene chloride, ether, tetrahydrofuran, dioxane, water or benzene, optionally in the presence of an acid-binding agent such as sodium carbonate, sodium hydroxide, triethylamine or pyridine, where the latter two may simultaneously also serve as solvents, preferably at temperatures between 0° and 100° C., for example at temperatures between room temperature and 50° C.

If the above methods yield a compound of the formula I wherein one of $R_1$, $R_2$ and $R_3$ is benzyloxy, this compound may be converted by debenzylation into the corresponding hydroxy compound; or If a compound of the formula I is obtained wherein at least one of $R_1$, $R_2$ and $R_3$ is cyano, this compound may be converted by hydrolysis into the corresponding aminocarbonyl compound; or If a compound of the formula I is obtained wherein at least one of $R_2$ and $R_3$ is nitro, this compound may be converted by reduction into the corresponding amino compound; or If a compound of the formula I is obtained wherein one of $R_1$, $R_2$ and $R_3$ is amino, this compound may be converted via its diazonium salt into a corresponding compound of the formula I wherein one of $R_1$, $R_2$ and $R_3$ is halogen, hydroxyl or cyano.

The subsequent debenzylation is preferably carried out in a solvent, such as water, water/ethanol, methanol, glacial acetic acid, ethyl acetate or dimethylformamide, with hydrogen in the presence of a hydrogenation catalyst such as Raney nickel, platinum or palladium-on-charcoal, at temperatures between 0° and 50° C., but preferably at room temperature.

The subsequent hydrolysis is carried out in the presence of an inorganic base with hydrogen peroxide, for instance with 2N sodium hydroxide or potassium hydroxide/hydrogen peroxide, at temperatures between 0° and 50° C., but preferably at room temperature.

The subsequent reduction of the nitro compound is preferably carried out in a solvent such as water, water/ethanol, methanol, glacial acetic acid, ethyl acetate or dimethylformamide, with hydrogen in the presence of a hydrogenation catalyst such as Raney nickel, platinum or palladium-on-charcoal with metals such as iron, tin or zinc in the presence of an acid, with salts such as iron(II)sulfate, tin(II)chloride or sodium dithionite or with hydrazine in the presence of Raney nickel at temperatures between 0° and 50° C., but preferably at room temperature.

The subsequent reaction of a diazonium salt, for example the fluoroborate, the fluoride in 40% hydrofluoric acid, the hydrosulfate in sulfuric acid or the hydrochloride, if necessary in the presence of copper or a corresponding copper(I) salt such as copper(I) chloride-hydrochloric acid or copper(I)hydrobromic acid, is carried out at slightly elevated temperatures, for instance at temperatures between 15° C. and 100° C. The required diazonium salt is advantageously prepared in a suitable solvent, for example in water/hydrochloric acid, methanol/hydrochloric acid, ethanol/hydrochloric acid or dioxane/hydrochloric acid, by diazotizing a corresponding amino compound with a nitrite, such as sodium nitrite or an ester of nitrous acid, at lower temperatures, for example at temperatures between −10° C. and 5° C.

The compounds embraced by formula I are basic and therefore form addition salts with inorganic or organic acids. Examples of non-toxic, pharmacologically acceptable acid addition salts are those formed wth hydrochloric, hydrobromic, sulfuric, phosphoric, fumaric, succinic, tartaric, citric, lactic, maleic or methanesulfonic acid.

The starting compounds of the formulas II to IX are either disclosed in the literature or may be prepared by methods described in the literature. For example, the starting compounds of the formula II are obtained by acylating the corresponding O-diamino compounds or by reducing the corresponding acylaminonitro compounds, and the compounds of the formulas III, IV, VI and VIII are obtained by subsequent cyclization (see British Pat. No. 810,545 and Published European Application No. 24,290) and optional subsequent debenzylation.

The following examples illustrate the present invention and will enable others skilled in the art to understand it more completely. It should be understood, however, that the invention is not limited solely to the particular examples given below.

EXAMPLE 1

2-(2,4-Dimethoxy-phenyl)-imidazo[4,5-c]pyridazine hydrochloride 2.7 g of 3,4-diamino-pyridazine hydrochloride were boiled for 0.5 hour in 10 ml of triethylamine. Excess triethylamine was drawn off, the residue was dissolved in 15 ml of glycol, and after the addition of 4.1 g of S-methyl-2,4-dimethoxy-thiobenzoic acid morpholide iodide the mixture was heated at 120° C. for 2 hours. The methylmercaptan formed thereby was removed in vacuo, the remaining solution was mixed with water, and the mixture was extracted several times with chloroform. The combined chloroform phases were evaporated, and the residue was purified by chromatography on silica gel (eluant: chloroform/methanol=100:0 to 100:3). The hydrochloride was precipitated by dissolving the residue in a little 2N hydrochloric acid and mixing the solution with concentrated hydrochloric acid.

Yield: 0.21 g (7% of theory).
M.p.: 245°–246° C. (decomposition).

EXAMPLE 2

2-(2-Methoxy-4-benzyloxy-phenyl)-imidazo[4,5-b]pyrazine

A mixture of 2.2 g of 2,3-diaminopyrazine and 5.16 g of 2-methoxy-4-benzyloxy-benzoic acid was finely triturated in a mortar and then suspended in 80 ml of phosphorus oxychloride. The suspension was refluxed for 1.5 hours while stirring. After cooling, the reaction mixture was mixed with ice water. The solution thus obtained was neutralized with ammonia and extracted with ethyl acetate. The ethyl acetate phases were evaporated, and the residue was triturated with acetone, whereupon the reaction product was left behind in pure form. A second fraction was obtained by evaporating the acetone phase and purifying the residue on silica gel (eluant: methylene chloride/ethanol=100:0 to 100:4).

Yield: 3.2 g (48% of theory).
M.p.: 178°–180° C.

EXAMPLE 3

2-(2-Methoxy-4-methanesulfonyloxy-phenyl)-imidazo[4,5-b]pyrazine (a)
2-(2-Methoxy-4-hydroxy-phenyl)-imidazo[4,5-b]pyrazine 3.15 g of 2-(2-methoxy-4-benzyloxy-phenyl)-imidazo[4,5-b]pyrazine were dissolved in 100 ml of methanol, and 2.6 g of 10% palladium-on-charcoal were added. The mixture was hydrogenated for 15 hours with hydrogen at 5 bar and at room temperature. The product precipitated thereby was suction-filtered off together with the catalyst. The solid residue was extracted with a mixture of equal parts of water and dimethylformamide. The extracts were combined with the above mother liquor, evaporated, and the crystalline residue was triturated with ether/acetone and suction-filtered.

Yield: 1.45 g (63% of theory).
M.p.: over 250° C.

(b)
2-(2-Methoxy-4-methanesulfonyloxy-phenyl)-imidazo[4,5-b]pyrazine 1.4 g of 2-(2-methoxy-4-hydroxy-phenyl)-imidazo[4,5-b]pyrazine were suspended in 40 ml of pyridine. 1.4 g of methanesulfonyl chloride dissolved in 10 ml pyridine were added dropwise to the mixture. The mixture was briefly heated to 40° C. and then stirred overnight at room temperature. The reaction mixture was poured into water and extracted with ethyl acetate. The ethyl acetate phases were evaporated, and the residue was stirred with 2N hydrochloric acid. The solid product thus obtained was recrystallized from 95 ml of ethanolic hydrochloric acid+5 ml of water.

Yield: 1.25 g (68% of theory).
M.p.: 207°–209° C.

EXAMPLE 4

2-(2,4-Dimethoxy-5-aminosulfonyl-phenyl)-imidazo[4,5-b]-pyrazine (a)

2-(2,4-Dimethoxy-5-chlorosulfonyl-phenyl)-imidazo-[4,5-b]pyrazine was prepared analogous to Example 2 from 2,3-diaminopyrazine and 2,4-dimethoxy-5-chlorosulfonyl-benzoylchloride.

M.p.: 294°–296° C.

(b)

2-(2,4-Dimethoxy-5-aminosulfonyl-phenyl)-imidazo[4,5-b]pyrazine 1.4 g of 2-(2,4-dimethoxy-5-chlorosulfonyl-phenyl-)imidazo[4,5-b]pyrazine were stirred for one hour with 25 ml of concentrated ammonia. The precipitate formed thereby was extracted with a boiling mixture of equal parts of acetone and ethanol.

Yield: 0.95 g (71% of theory).
M.p.: 250°–252° C.

EXAMPLE 5

2-(2-Methoxy-4-methylsulfonyl-phenyl)-imidazo[4,5-b]-pyrazine 0.7 g of 2-(2-methoxy-4-methylmercapto-phenyl)-imidazo-[4,5-b]pyrazine were suspended in 28 ml of 90% acetic acid, and the suspension was mixed with 0.45 ml of 30% hydrogen peroxide. Hydrochloric acid was then added until a clear solution was formed. This solution was allowed to stand overnight and the precipitate formed thereby was suction-filtered off. It was then boiled with methanolic hydrochloric acid, suction-filtered off and washed with acetone and ether.

Yield: 0.42 g (58% of theory).
M.p.: 273°–276° C.

EXAMPLE 6

2-(2-Methoxy-4-methyl-phenyl)-imidazo[4,5-d]pyridazine hydrochloride

This compound was prepared analogous to Example 1 from 4,5-diamino-pyridazine and S-methyl-2-methoxy-4-methyl-thiobenzoic acid morpholide.

M.p.: 216°–218° C. (decomposition).

EXAMPLE 7

2-(2-Methoxy-4-methanesulfonylamino-phenyl)-imidazo[4,5-b]pyrazine

This compound was prepared analogous to Example 2 from 2,3-diamino-pyrazine and 2-methoxy-4-methanesulfonylaminobenzoic acid.

M.p.: 263°–265° C.

EXAMPLE 8

2-(2-Methoxy-4-methanesulfonyloxy-phenyl)-imidazo[4,5-e]1,2,4-triazine

This compound was prepared from 0.75 g of 2-(2-methoxy-4-hydroxy-phenyl)-imidazo[4,5-e]1,2,4-triazine and 1 ml methanesulfonyl chloride in a mixture of 25 ml of pyridine and 2 ml of 2N sodium hydroxide solution, by heating the reaction mixture at 50° C. for 10 hours. The mixture was worked up by evaporating the solvent, mixing the residue with ice water and purifying the precipitated crude product on silica gel (eluant: methylene chloride/ethanol=50:1 to 25:1).

Yield: 0.08 g (21% of theory).
M.p.: 217°–219° C.

EXAMPLE 9

2-(2-Methoxy-4-cyanomethoxy-phenyl)-imidazo[4,5-e]-1,2,4-triazine

This compound was prepared from the potassium salt of 2-(2-methoxy-4-hydroxy-phenyl)-imidazo[4,5-e]-1,2,4-triazine and chloroacetonitrile.

EXAMPLE 10

2-(2-Methoxy-4-propargyloxy-phenyl)-imidazo[4,5-e]-1,2,4-triazine

This compound was prepared analogous to Example 9 from the potassium salt of 2-(2-methoxy-4-hydroxy-phenyl)-imidazo[4,5-e]-1,2,4-triazine and propargyl bromide.

M.p.: 227°–230° C.

EXAMPLE 11

2-(2-Methoxy-4-methanesulfonyloxy-phenyl)-imidazo[4,5-d]pyridazine

This compound was prepared analogous to Example 3(b) from 2-(2-methoxy-4-hydroxy-phenyl)-imidazo[4,5-d]pyridazine.

M.p.: 202°–204° C. (decomposition).

EXAMPLE 12

2-(2-Methoxy-4-methanesulfonylamino-phenyl)-imidazo[4,5-d]pyridazine

This compound was prepared analogous to Example 3(b) from 2-(2-methoxy-4-amino-phenyl)-imidazo[4,5-d]pyridazine.

M.p.: 253A°–254° C. (decomposition).

EXAMPLE 13

2-(2-Methoxy-4-methylsulfonyl-phenyl)-imidazo[4,5-d]pyridazine

This compound was prepared by oxidation of 2-(2-methoxy-4-methyl-mercapto-phenyl)-imidazo[4,5-d]pyridazine with hydrogen peroxide in glacial acetic acid.

EXAMPLE 14

2-(2-Methoxy-4-aminosulfonyl-phenyl)-imidazo[4,5-d]pyridazine

This compound was prepared analogous to Example 4(b) from 2-(2-methoxy-4-chlorosulfonyl-phenyl)-imidazo[4,5-d]pyridazine.

M.p.: 228°–230° C.

EXAMPLE 15

2-(2-Methoxy-4-aminosulfonyl-phenyl)-imidazo[4,5-d]pyridazine

This compound was prepared analogous to Example 4(b) from 2-(2-methoxy-4-chlorosulfonyl-phenyl)-imidazo[4,5-d]pyridazine and aqueous methylamine solution.

M.p.: 245°–246° C.

EXAMPLE 16

2-(2-Methoxy-4-dimethylaminosulfonyl-phenyl)-imidazo[4,5-d]pyridazine

This compound was prepared analogous to Example 4(b) from 2-(2-methoxy-4-chlorosulfonyl-phenyl)-imidazo[4,5-d]pyridazine and aqueous dimethylamine solution.

M.p.: 219°–220° C.

EXAMPLE 17

2-(2-Methoxy-4-cyano-phenyl)-imidazo[4,5-d]pyridazine

This compound was prepared from 2-(2-methoxy-4-aminophenyl)-imidazo[4,5-d]pyridazine by diazotizing and subsequent reaction with copper (I) cyanide.

EXAMPLE 18

2-(2-Methoxy-4-aminocarbonyl-phenyl)-imidazo[4,5-d]pyridazine

This compound was prepared from 2-(2-methoxy-4-cyanophenyl)imidazo[4,5-d]pyridazine by partial hydrolysis with alkaline hydrogen peroxide.

EXAMPLE 19

2-(2-Dimethylamino-4-nitro-phenyl)-imidazo[4,5-e]-1,2,4-triazine

This compound was prepared analogous to Example 2 from 5,6-diamino-1,2,4-triazine and 2-dimethylamino-4-nitrobenzoic acid.

EXAMPLE 20

2-(2-Dimethylamino-4-amino-phenyl)-imidazo[4,5-e]-1,2,4-triazine

This compound was prepared by reduction of 2-(2-dimethylamino-4-nitro-phenyl)-imidazo[4,5-e]-1,2,4-triazine with hydrogen in the presence of palladium-on-charcoal in glacial acetic acid.

EXAMPLE 21

2-(2-Dimethylamino-4-acetylamino-phenyl)-imidazo[4,5-e]-1,2,4-triazine

This compound was prepared from 2-(2-dimethylamino-4-amino-phenyl)-imidazo[4,5-e]-1,2,4-triazine by heating with acetic acid anhydride.

EXAMPLE 22

2-(2-Dimethylamino-4-methanesulfonylamino-phenyl)-imidazo[4,5-e]-1,2,4-triazine

This compound was prepared analogous to Example 3(b) from 2-(2-dimethylamino-4-amino-phenyl)-imidazo[4,5-e]-1,2,4-triazine.

EXAMPLE 23

2-(2-Methoxy-4-methylmercapto-phenyl)-imidazo[4,5-c]-pyridazine

This compound was prepared analogous to Example 2 from 3,4-diamino-pyridazine and 2-methoxy-4-methylmercapto-benzoic acid.

M.p.: 190°–192° C. (decomposition).

EXAMPLE 24

2-(2-Methoxy-4-methylsulfinyl-phenyl)-imidazo[4,5-c]-pyridazine

This compound was prepared analogous to Example 13 from 2-(2-methoxy-4-methylmercapto-phenyl)-imidazo[4,5-c]pyridazine.

M.p. 213°–215° C. (decomposition).

EXAMPLE 25

2-(2-Methoxy-4-methylsulfonyl-phenyl)-imidazo[4,5-c]-pyridazine

This compound was prepared analogous to Example 13 from 2-(2-methoxy-4-methylmercapto-phenyl-imidazo[4,5-c]pyridazine.

M.p.: 196°–198° C. (decomposition).

EXAMPLE 26

2-(2-Methoxy-4-methanesulfonyloxy-phenyl)-imidazo[4,5-c]pyridazine

This compound was prepared from 0.28 g of 2-(2-methoxy-4-hydroxy-phenyl)-imidazo[4,5-c]pyridazine and 0.52 g of methanesulfonyl chloride in a solution of 0.21 g of sodium hydroxide in 100 ml of water by stirring for 2 days at room temperature.

Yield: 0.2 g (55% of theory).

M.p.: 215°–217° C. (decomposition).

EXAMPLE 27

2-(2-Methoxy-4-chloro-phenyl)-imidazo[4,5-e]-1,2,4-triazinehydrochloride

This compound was prepared from 0.2 g of 5,6-diamino-1,2,4-triazine hydrochloride and 0.25 g of 2-methoxy-4-chlorobenzoic acid by heating for 3 hours to 105°–120° C. in 25 g of polyphosphoric acid.

Yield: 0.65 g (16% of theory).

M.p.: 220°–222° C.

EXAMPLE 28

2-(2-Methoxy-4-methylmercapto-phenyl)-imidazo[4,5-e]-1,2,4-triazine

This compound was prepared analogous to Example 2 from 5,6-diamino-1,2,4-triazine and 2-methoxy-4-methylmercaptobenzoic acid.

M.p.: 240°–241° C.

EXAMPLE 29

2-(2-Methoxy-4-methylsulfinyl-phenyl)-imidazo[4,5-e]-1,2,4-triazine

This compound was prepared from 2-(2-methoxy-4-methylmercapto-phenyl)-imidazo[4,5-e]-1,2,4-triazine by oxidation with bromine in acetic acid in the presence of sodium acetate.

EXAMPLE 30

2-(2-Methoxy-4-methylsulfonyl-phenyl)-imidazo[4,5-e]-1,2,4-triazine

This compound was prepared analogous to Example 13 from 2-(2-methoxy-4-methylmercapto-phenyl)-imidazo[4,5-e]-1,2,4-triazine.

M.p.: 261°–264° C.

EXAMPLE 31

2-(2-Methoxy-4-dimethylaminosulfonyl-phenyl)-imidazo[4,5-c]pyridazine

This compound was prepared analogous to Example 27 from 3,4-diamino-pyridazine hydrochloride and 2-methoxy-4-dimethylaminosulfonyl-benzoic acid.
M.p.: 220°–225° C.

EXAMPLE 32

2-(2-Methoxy-4-benzyloxy-phenyl)-imidazo[4,5-c]pyridazine

This compound was prepared analogous to Example 2 from 3,4-diamino-pyridazine hydrochloride and 2-methoxy-4-benzyloxybenzoic acid.
M.p.: 196°–197° C.

EXAMPLE 33

2-(2-Methoxy-4-amino-phenyl)-imidazo[4,5-d]pyridazine

This compound was prepared analogous to Example 27 from 3,4-diaminopyridazine and 2-methoxy-4-aminobenzoic acid.
M.p.: 270°–271° C.

EXAMPLE 34

2-(2-Methoxy-4-chloro-phenyl)-imidazo[4,5-d]pyridazine

This compound was prepared from 2-(2-methoxy-4-aminophenyl)-imidazo[4,5-d]pyridazine by diazotizing in concentrated hydrochloric acid and exchanging the diazonium group in the presence of copper(I) chloride.
M.p.: 260°–262° C.

EXAMPLE 35

2-(2-Methoxy-4-propargyloxy-phenyl)-imidazo[4,5-e]-1,2,4-triazine

This compound was prepared analogous to Example 2 from 2-methoxy-4-propargyloxy-benzoic acid and 5,6-diamino-1,2,4-triazine.
M.p.: 227°–230° C.

EXAMPLE 36

2-(2-Methoxy-4-aminocarbonyl-phenyl)-imidazo[4,5-c]pyridazine

This compound was prepared analogous to Example 27 from 3,4-diaminopyridazine hydrochloride and 2-methoxy-4-cyanobenzoic acid.
M.p.: 275°–285° C. (decomposition), then resolidification and melting at 315°–323° C. (decomposition).

The compounds of the present invention, that is, those embraced by formula I above, their tautomers and their non-toxic, pharmacologically acceptable acid addition salts, have useful pharmacodynamic properties. More particularly, they exhibit hypotensive and positive inotropic activites in warm-blooded animals such as cats.

The above pharmacological properties were ascertained for the compounds of the present invention by the standard pharmacological test method described below, and the results of this test for two representative species of the genus are shown in the table below, where A = 2-(2-methoxy-4-methanesulfonyloxy-phenyl)-imidazo[4,5-b]pyrazine, and B = 2-(2-Methoxy-4-methanesulfonyloxy-phenyl)-imidazo[4,5-d]pyridazine.

Determination of the effect on blood pressure and of the positive inotropic effect in the anesthetized cat The tests were carried out on cats which had been anesthetized with sodium pentobarbital (40 mg/kg i.p.). The animals breathed spontaneously. The arterial blood pressure was measured in the aorta abdominalis with a Statham pressure transducer (P 23 Dc). In order to determine the positive inotropic activity, the pressure in the left ventricle was measured with a catheter-tip manometer (Millar PC-350 A). From this the contractility parameter dp/dt was obtained, using an analog differentiator. The test compounds were injected into a vena femoralis. Polydiol 200 was used as the solvent. Each compound was tested on at least 3 cats.

The following Table shows the average values:

| Compound | Dosage mg/kg | Increase in $dp/dt_{max}$ in % | Effect on blood pressure in mm Hg | Duration of activity (half life) in minutes |
|---|---|---|---|---|
| A | 0.6 | 54 | −24/−21 | 20 |
| B | 0.3 | 36 | −31/−18 | 38 |

The compounds of the present invention are well tolerated, and no toxic effects on the heart or damage to the circulation of any kind were detected in these tests.

Based on their pharmacological properties the compounds of the present invention are useful for the treatment of cardiac insufficiencies of various origins since they increase the contractile force of the heart and facilitate the emptying of the heart by additionally lowering the blood pressure.

For pharmaceutical purposes the compounds of the present invention are administered to warm-blooded animals perorally, parenterally or rectally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories and the like. An effective amount of the compounds according to the present invention is from 0.1 to 5 mg/kg bodyweight, one to four times daily.

The following examples illustrate a few pharmaceutical dosage unit compositions comprising a compound of the present invention as an active ingredient and represent the best modes contemplated of using the invention. The parts are parts by weight unless otherwise specified.

EXAMPLE 37

Tablets

The tablet composition is compounded from the following ingredients:

| | |
|---|---|
| 2-(2-Methoxy-4-methanesulfonyloxy-phenyl)imidazo[4,5-b]pyrazine | 100.0 parts |
| Lactose | '50.0 parts |
| Polyvinyl pyrrolidone | 5.0 parts |
| Carboxymethyl cellulose | 19.0 parts |
| Magnesium stearate | 1.0 parts |
| | 175.0 parts |

Preparation:
Moist screen: 1.5 mm.
Drying: circulating air drier, 50° C.
Dry screen: 1 mm.
The remaining excipients are added to the granulate, and the finished mixture is compressed into 175 mg-tablets. Each tablet contains 100 mg of the active ingredient.

EXAMPLE 38

Coated tablets
The tablet core composition is compounded from the following ingredients:

| | |
|---|---|
| 2-(2-Methoxy-4-methanesulfonyloxy-phenyl)imidazo[4,5-b]pyrazine | 50.0 parts |
| Dried corn starch | 20.0 parts |
| Soluble starch | 2.0 parts |
| Carboxymethyl cellulose | 7.0 parts |
| Magnesium stearate | 1.0 parts |
| | 80.0 parts |

Preparation:
The active ingredient and the corn starch are uniformly moistened with an aqueous solution of the soluble starch.
Moist screen: 1.0 mm.
Dry screen: 1.0 mm.
Drying: 50° C. in a circulating air drier. The granulate and other excipients are mixed together and compressed into 80 mg-tablet cores.
The finished cores are provided with a sugar coating in a coating pan in the usual way. Weight of the coated tablet: 120 mg. Each coated tablet contains 50 mg of the active ingredient.

EXAMPLE 39

Suppositories
The suppository composition is compounded from the following ingredients:

| | |
|---|---|
| 2-(2-Methoxy-4-methanesulfonyloxy-phenyl)-imidazo[4,5-b]pyrazin | 75.0 parts |
| Suppository base (e.g. cocoa butter) | 1625.0 parts |
| | 1700.0 parts |

Preparation:
The suppository base is melted. At 38° C. the finely ground active ingredient is homogeneously dispersed in the melt. The composition is cooled to 35° C., and 1700 mg-portions of it are poured into chilled suppository molds. Each suppository contains 75 mg of the active ingredient.

EXAMPLE 40

Hypodermic solution
The solution is compounded from the following ingredients:

| | | |
|---|---|---|
| 2-(2-Methoxy-4-methanesulfonylxoy-phenyl)-imidazo[4,5-b]pyrazine | | 50.0 parts |
| Ethoxylated hydroxystearic acid | | 750.0 parts |
| 1,2-Propylene glycol | | 1000.0 parts |
| Distilled water | ad | 5000.0 parts by vol. |

Preparation:
The active ingredient is dissolved in 1,2-propylene glycol and ethoxylated hydroxystearic acid, the solution is diluted to the indicated volume with water, and filtered sterile.
Filling: in 5 ml ampules.
Sterilization: 20 minutes at 120° C.

EXAMPLE 41

Drop solution
The solution is compounded from the following ingredients:

| | | |
|---|---|---|
| 2-(2-Methoxy-4-methanesulfonyl-phenyl)-imidazo[4,5-b]pyrazine | | 1.0 parts |
| Methyl p-hydroxybenzoate | | 0.035 parts |
| Propyl p-hydroxybenzoate | | 0.015 parts |
| Anisole | | 0.05 parts |
| Menthol | | 0.06 parts |
| Sodium saccharin | | 1.0 parts |
| Glycerol | | 10.0 parts |
| Ethanol | | 40.0 parts |
| Distilled water | ad | 100.0 parts by vol. |

Preparation:
The benzoates are dissolved in ethanol, and then the anisole and menthol are added. Then the active ingredient, glycerin and sodium saccharin dissolved in water are added. The solution is then filtered clear.

Any one of the other compounds embraced by formula I, a tautomer thereof or a non-toxic, pharmacologically acceptable acid addition salt thereof may be substituted for the particular active ingredient in Examples 37 through 41. Likewise, the amount of active ingredient in these illustrative examples may be varied to achieve the dosage unit range set forth above, and the amount and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the formula

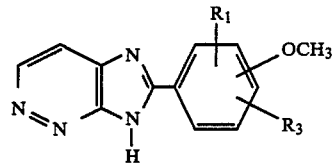

or

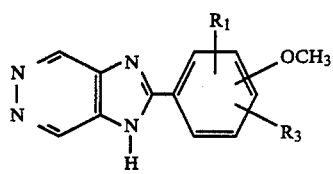

wherein
$R_1$ is methanesulfonyloxy, methanesulfonylamino, N-methylmethanesulfonylamino, aminosulfonyl, methylaminosulfonyl or dimethylaminosulfonyl; and R₃ is hydrogen or methoxy;
a tautomer thereof; or a non-toxic, pharmacologically acceptable acid addition salt thereof.

2. A compound of claim 1,
where
R₁ is methanesulfonyloxy, aminosulfonyl, methylaminosulfonyl or dimethylaminosulfonyl; and
R₃ is hydrogen or methoxy;
a tautomer thereof; or a non-toxic, pharmacologically acceptable acid addition salt thereof.

3. A compound of claim 1, which is of the formula

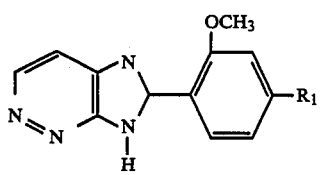

or

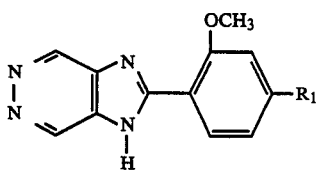

wherein R₁ is methanesulfonyloxy, aminosulfonyl, methylaminosulfonyl or dimethylaminosulfonyl;
a tautomer thereof; or a non-toxic, pharmacologically acceptable acid addition salt thereof.

4. A compound of claim 1 of the formula

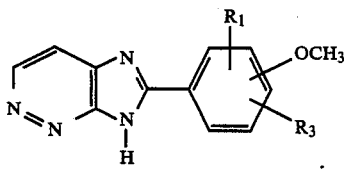

wherein
R₁ is methanesulfonyloxy, methanesulfonylamino, N-methylmethanesulfonylamino, aminosulfonyl, methylaminosulfonyl or dimethylaminosulfonyl; and
R₃ is hydrogen or methoxy;
a tautomer thereof; or a non-toxic, pharmacologically acceptable acid addition salt thereof.

5. A compound of claim 4,
where
R₁ is methanesulfonyloxy, aminosulfonyl, methylaminosulfonyl or dimethylaminosulfonyl; and
R₃ is hydrogen or methoxy;
a tautomer thereof; or a non-toxic, pharmacologically acceptable acid addition salt thereof.

6. A compound of claim 1 of the formula

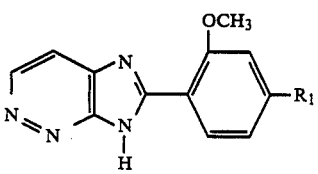

wherein R₁ is methanesulfonyloxy, aminosulfonyl, methylaminosulfonyl or dimethylaminosulfonyl;
a tautomer thereof; or a non-toxic, pharmacologically acceptable acid addition salt thereof.

7. A compound of claim 6, which is 2-(2-methoxy-4-methanesulfonyl-oxy-phenyl)-imidazo[4,5-c]pyridazine; a tautomer thereof; or a non-toxic, pharmacologically acceptable acid addition salt thereof.

8. A compound of claim 1 of the formula

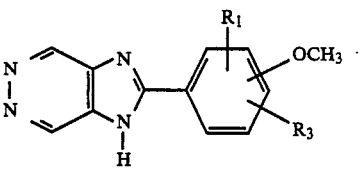

wherein
R₁ is methanesulfonyloxy, methanesulfonylamino, N-methylmethanesulfonylamino, aminosulfonyl, methylaminosulfonyl or dimethylaminosulfonyl; and
R₃ is hydrogen or methoxy;
a tautomer thereof; or a non-toxic, pharmacologically acceptable acid addition salt thereof.

9. A compound of claim 8,
where
R₁ is methanesulfonyloxy, aminosulfonyl, methylaminosulfonyl or dimethylaminosulfonyl; and
R₃ is hydrogen or methoxy;
a tautomer thereof; or a non-toxic, pharmacologically acceptable acid addition salt thereof.

10. A compound of claim 9 of the formula

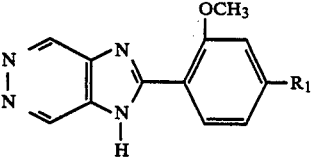

wherein R₁ is methanesulfonyloxy, aminosulfonyl, methylaminosulfonyl or dimethylaminosulfonyl;
a tautomer thereof; or a non-toxic, pharmacologically acceptable acid addition salt thereof.

11. A compound of 10, which is 2-(2-methoxy-4-methanesulfonyl-oxy-phenyl)-imidazo[4,5-d]pyridazine; a tautomer thereof; or a non-toxic, pharmacologically acceptable acid addition salt thereof.

12. A cardiotonic pharmaceutical composition consisting essentially of an inert pharmaceutical carrier and an effective cardiotonic amount of a compound of claim 1.

13. The method of treating cardiac insufficiency in a warm-blooded animal in need thereof, which comprises administering to said animal an effective amount of a compound of claim 1.

* * * * *

UNITED STATES PATENT AND TRADEMARK OFFICE
CERTIFICATE OF CORRECTION

PATENT NO. : 4,746,658

DATED : May 24, 1988

INVENTOR(S) : Austel et al.

It is certified that error appears in the above-identified patent and that said Letters Patent is hereby corrected as shown below:

Col. 10, line 40 - "253A°" should read -- 253°C --.

Col. 15, line 60 - "methanesulfonylxoy" should read
 -- methanesulfonyloxy --.

Signed and Sealed this

Eighteenth Day of October, 1988

Attest:

DONALD J. QUIGG

*Attesting Officer*   *Commissioner of Patents and Trademarks*